(12) United States Patent
Gergely et al.

(10) Patent No.: US 6,572,877 B2
(45) Date of Patent: Jun. 3, 2003

(54) WORM FOOD COMPOSITION

(75) Inventors: Lane F. Gergely, Seguin, TX (US); Anthony J. Gergely, Seguin, TX (US)

(73) Assignee: Legend Laboratories Corporation, Seguin, TX (US)

( * ) Notice: Subject to any disclaimer, the term of this patent is extended or adjusted under 35 U.S.C. 154(b) by 34 days.

(21) Appl. No.: 09/881,350

(22) Filed: Jun. 14, 2001

(65) Prior Publication Data

US 2002/0193426 A1 Dec. 19, 2002

(51) Int. Cl.[7] ............................................. A01K 67/033
(52) U.S. Cl. ...................... 424/442; 424/405; 424/410; 424/9.8; 514/454; 119/6.7
(58) Field of Search .............................. 514/454; 426/1, 426/645; 424/405, 410, 9.8; 119/6.7, 230

(56) References Cited

U.S. PATENT DOCUMENTS 2,849,981 A  *  9/1958  Rose et al. ..................... 119/1
6,240,876 B1 *  6/2001  Giannaris ..................... 119/6.7

* cited by examiner

*Primary Examiner*—Neil S. Levy
(74) *Attorney, Agent, or Firm*—Gunn, Lee & Hanor, P.C.; Michelle Evans

(57) ABSTRACT

A food composition for feeding to worms to enhance their desirability to predators and process therefor is disclosed. The composition contains a xanthene dye which is applied to the surface of or admixed with a nutritionally acceptable carrier in an amount sufficient to enhance the worm's detection by the visual color receptors of a fish.

7 Claims, No Drawings

WORM FOOD COMPOSITION

BACKGROUND OF THE INVENTION

1. Field of the Invention

Applicant's invention relates to a food composition for feeding to worms to enhance their desirability to predators, particularly fish, and the process therefor.

2. Background Information

There are many factors that play a part in enhancing the desirability of worms to predators, such as fish. Researchers have found that fish possess both rod and cone cells in their eyes. This results in their ability to see color and their sensitivity to various shades of light. Therefore, a fish's ability to detect prey, such as worms, can be affected by the water clarity. In conditions where sediment is high, visibility is drastically reduced. Thus, particularly in such conditions, color can play a major role in the fish's ability to both see and strike its prey.

Movement or activity of the prey is also critical in the fish's ability to successfully feed. Therefore healthy prey, such as a worm that shows more activity on the hook, will create more attention and receive more strikes by fish. Where worms are used as prey, the temperature at which the worms are kept can be crucial to their activity. The optimum temperature to maintain the activity of worms varies by the genus. In addition, the nourishment of the worm can play a critical role in the activity of the worm. A weak, malnourished worm will not be active even if temperatures are suitable. Worms kept at a suitable temperature and provided adequate nutriment will vigorously feed resulting in increased activity thereby enhancing a fish's ability to successfully feed. The nutriment over time also increases the size of the worm which further aids in the fish's ability to detect the prey.

From this data it was determined that worms that have enhanced visual detectability, are both large and active, and that maintain a suitable shelf life will provide the optimum bait for the fishing industry. As there are no known worm food compositions on the market that provide for these combined benefits, it was the desire of the present Applicants to satisfy this long felt need in the industry by providing for a worm food composition having a nutritious food mass and a xanthene dye. This worm food composition enhances the visual detectability of the worm to predators, enhances the growth and activity of the worm, and enhances the health of the worm which contributes to an increased life span in captivity to maintain a suitable shelf life.

SUMMARY OF THE INVENTION

It is an object of the present invention to provide a novel food composition for feeding to worms to enhance their desirability to predators, particularly fish, and process therefor.

Still another object of the present invention is to provide a novel food composition for feeding to worms to increase their activity in the water.

Another object of the present invention is to provide a novel food composition for feeding to worms to increase their size.

Yet another object of the present invention is to provide a novel food composition for feeding to worms to enhance their reception by the visual color receptors of a predator, such as a fish.

It is another object of the present invention to provide a novel food composition for feeding to worms to increase their life span in captivity.

An additional object of the present invention is to provide for a novel food composition for feeding to worms so the worms can maintain a suitable shelf life.

Still another object of the present invention is to provide a novel food composition for feeding to worms that incorporates a xanthene dye.

It is another object of the present invention to provide a novel food composition for feeding to worms that incorporates a hydroxyl substituted xanthene.

Another object of the present invention is to provide for a novel food composition for feeding to worms that incorporates fluoroscein.

Yet another object of the present invention is to provide for a novel method for enhancing the desirability of worms to predators by feeding the worms the food composition of the present invention.

In satisfaction of these and related objectives, Applicant's present invention provides a food composition for feeding to worms to enhance their desirability to predators and process therefor.

DETAILED DESCRIPTION OF THE PREFERRED EMBODIMENT

The preferred embodiment of the present invention is a food composition for feeding to worms which contains a nutritious food mass and a xanthene dye. The nutritious food mass is preferably a grain including corn meal, cottonseed meal, rice bran, wheat bran, Milo, and any other grain suitable to a worm's diet. The nutritious food mass may also include other worm food sources, such as spirulina algae.

Xanthene dyes are those containing the xanthylium or dibenzo-γ-pyran (xanthene) nucleus.

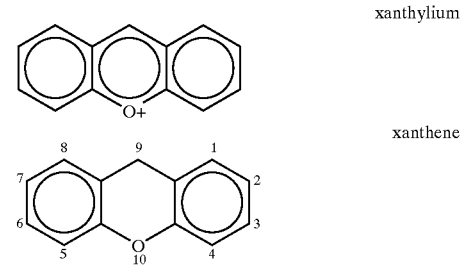

These dyes have brilliant hues in the shade range of greenish yellows to dark violets and blues, and they exhibit fluorescence. Such dyes are known to be used for the dyeing of wool, silk, paper, leather, woods, food, drugs and cosmetics. Xanthene dyes are classified into three groups according to the nature of the aromatic substitution: amino derivatives, hydroxy derivatives, and aminohydroxy derivatives. An amino derivative xanthene dye, such as rhodamine and most preferably Rhodamine B ($C_{28}H_{31}N_2O_3Cl$), may be used in the present invention. However, the present invention preferably incorporates a hydroxy derivative xanthene dye. The building blocks of most hydroxyl-substituted xanthenes, or fluorones, is fluorescein.

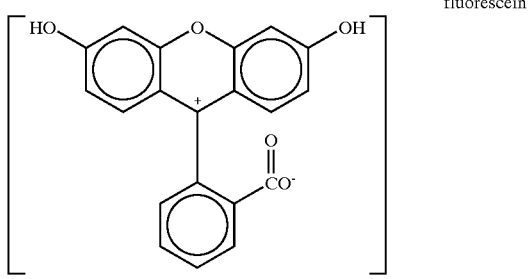

fluorescein

The xanthene dye of the present invention is preferably xanthene acid yellow 73 ($C_{20}H_{10}Na_2O_5$). Xanthene acid yellow 73 in particular is known to be used as an analytical reagent to label protein and as a clinical reagent as an immuno-histological stain and immuno-fluorescent label. It may be applied to the surface of or admixed with the nutritious food mass after manufacture of the nutritious food mass, in an amount sufficient to enhance the worm's detection by the visual color receptors of a fish. The preferred embodiment of the present invention utilizes the xanthene dye generally in an amount of at least about 2.44% by weight, being generally about 4.76% by weight and preferably about 2.44% to 11.11% by weight of the nutritious food mass.

In experiments conducted using the food composition of the present invention, it was determined that the food composition not only made the worms visually enhanced for detection by fish, but also increased the worms activity and size and notably enhanced their life span in captivity. In conducting the research into color change, size, and mobility, three types of earthworms were used. These worms were (1) *Lumbricus terrestris,* commonly known as the Canadian night crawler, (2) *Eisenia hortensis,* commonly known as the European night crawler, and (3) *Eisenia foetida,* commonly referred to as the red wiggler. Each of these worms belong to kingdom Animalia, phylum Annelida, subphylum Aclitellata, class Oligochaeta, order Opisthopora, suborder Lumbricina, superfamily Lumbricoidea, and family Lumbricidae.

The first experiment was conducted with *Lumbricus terrestris. Lumbricus terrestris* typically measures from 90–300 mm by 6–10 mm having a dark anterior and a pale flattened posterior. These worms live in an anecic habit meaning that they build permanent, vertical burrows that extend typically 2.5 m into the soil. Such worms feed in decaying organic material and grow and breed very slowly compared to other worms. This worm must have the burrow to return to and simply won't perform well in a worm bin. In their natural habitat such worms can live up to six years.

In the experiment, five cartons containing one dozen worms plus bedding each were kept in the refrigerator at 36° F. to 40° F. prior to the beginning the experiment. After refrigeration the following compounds were added to the specified cartons. Carton 1 was treated with a stock solution of 5 ml xanthene acid yellow 73 from a stock solution of 0.5 g xanthene acid yellow 73 in 500 ml distilled water. Carton 2 was treated with 5 grams of a stock mixture having 40 grams corn meal and 1 gram xanthene acid yellow 73. This mixture was simply added to Carton 2 and was not agitated. Carton 3 was treated with 5 grams of the same stock mixture and shaken gently to evenly disperse the mixture in Container 3. Carton 4 was treated with 5 grams from a mixture of 40 grams corn meal and 2 grams xanthene acid yellow 73 and was not agitated. Carton 5 was treated with the same stock mixture and shaken gently to evenly disperse the mixture in the container.

Carton 1 showed no change in the color of the worm even after 7 days. Carton 2 showed some coloration at 5–7 days and the worms were larger and more active than the worms in Carton 1. After six weeks the worms in Carton 1 were weak and dying from lack of nutrition whereas the worms in Carton 2 still showed coloration and remained fat and active. Carton 3 had the same coloration as Carton 2 and the worms were fat and active. The worms in Cartons 4 and 5 were identical in appearance exhibiting a coloration change to a pale yellow to pale green (chartreuse) and were extremely fat and active. In Carton 5 an additional 5 grams of the stock mixture containing 40 grams corn meal and 2 grams xanthene acid yellow 73 was added at 3.5 weeks. With these worms it is preferred that reapplication of the food composition be given every four weeks to ensure the worms are being fed.

The second worm tested with the food composition of the present invention was *Eisenia hortensis. Eisenia hortensis* is hardier than the Lumbricus terrestris and is an epigeic or compost worm that is found on the surface. Grain feeding works well for this species but it is somewhat sensitive to pH requiring an optimum pH around 6.0–7.0. The natural life span of *E. hortensis* is only over a year.

Several cartons were used in the experiment containing 24 worms per container plus bedding. These worms were kept at a room temperature of 70° F. to 80° F. The worms were fed 5 grams of a stock mixture containing 6.25 grams xanthene acid yellow 73 in 100 grams ground corn meal. These worms were significantly dyed to a splendid chartreuse color in 24 to 48 hours. These worms were also used to determine whether the dye is absorbed through the skin or ingested by the worms. *E. hortensis* actively feed at 70° F. to 80° F. Therefore, to determine whether the dye is absorbed through the skin or ingested by the worms, 5 grams of the stock mixture containing 6.25 grams xanthene acid yellow 73 in 100 grams ground corn meal was added to another carton and then the carton was refrigerated for one week. No coloration or size change occurred therefore it was determined that the dye must be ingested along with the food rather than absorbed through the skin.

The next worm used in the experimentation was *Eisenia foetida,* the common red wiggler. This worm is specially adapted to a worm bin environment and tolerates a wide range of environmental conditions. *E. fetida* is also an epigeic worm which means that it builds no permanent burrows and prefers an environment of organic debris to that of soil. This worm feeds in decaying organic matter and has a short life span.

One carton of *E. fetida* was obtained containing 24 worms with bedding. These worms were kept at 70° F. to 80° F. The food composition of the present invention was applied in an amount of 5 grams from a stock mixture of 6.25 grams xanthene acid yellow 73 and 100 grams ground corn meal. The worms significantly changed to chartreuse in 5 days and were very active and larger than they were when the experiment began.

From these experiments it was determined that the food composition of the present invention will provide a significant advantage to the fishing and bait industry by enhancing the visual detectability of the worm, enhancing the size and activity of the worm, and maintaining a suitable shelf life for the worm. This composition also allows for ease of application in that it can be either distributed on top of the worm's bedding or mixed throughout. It is believed that this food composition can be modified within obvious parameters to be used for feeding other forms of bait such as, but not limited to, mealworms, wax worms, shrimp, and baitfish.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A method of coloring live worms which increases the growth and activity of the worms and increases their life span in captivity, comprising the step of feeding a food composition to said worms comprising a nutritious food mass and a visual detection enhancing amount of a xanthene dye of at least 2.44% by weight of said food composition.

2. The method of coloring live worms which increases the growth and activity of the worms and increases their life span in captivity of claim 1 further comprising the step of distributing said food composition over said worm's bedding.

3. The method of coloring live worms which increases the growth and activity of the worms and increases their life span in captivity of claim 1 further comprising the step of mixing said food composition throughout said worm's bedding.

4. The method of coloring live worms which increases the growth and activity of the worms and increases their life span in captivity of claim 1 wherein said xanthene dye is a hydroxyl substituted xanthene.

5. The method of coloring live worms which increases the growth and activity of the worms and increases their life span in captivity of claim 4 wherein said xanthene dye is fluoroscein.

6. The method of coloring live worms which increases the growth and activity of the worms and increases their life span in captivity, of claim 5 wherein said xanthene dye is xanthene acid yellow 73.

7. The method of coloring live worms which increases the growth and activity of the worms and increases their life span in captivity of claim 6 wherein said nutritious food mass is grain.

* * * * *